US008157783B2

(12) United States Patent
Yoshikawa

(10) Patent No.: US 8,157,783 B2
(45) Date of Patent: Apr. 17, 2012

(54) MEDICAL LIQUID CONTAINER

(75) Inventor: Katsuyuki Yoshikawa, Ichihara (JP)

(73) Assignee: Hosokawa Yoko Co., Ltd., Tokyo (JP)

(*) Notice: Subject to any disclaimer, the term of this patent is extended or adjusted under 35 U.S.C. 154(b) by 298 days.

(21) Appl. No.: 11/579,325

(22) PCT Filed: May 31, 2005

(86) PCT No.: PCT/JP2005/010297

§ 371 (c)(1), (2), (4) Date: Nov. 1, 2006

(87) PCT Pub. No.: WO2005/117801

PCT Pub. Date: Dec. 15, 2005

(65) Prior Publication Data

US 2008/0255535 A1 Oct. 16, 2008

(30) Foreign Application Priority Data

Jun. 21, 2004 (JP) ................................ P2004-164770

(51) Int. Cl.
*A61B 19/00* (2006.01)

(52) U.S. Cl. ........ 604/410; 604/408; 604/409; 604/411; 206/219; 206/484; 383/107; 383/109

(58) Field of Classification Search ........... 604/408–411
See application file for complete search history.

(56) References Cited

U.S. PATENT DOCUMENTS

| | | | | |
|---|---|---|---|---|
| 4,997,083 | A | 3/1991 | Loretti et al. | |
| 5,462,526 | A * | 10/1995 | Barney et al. | 604/85 |
| 5,853,388 | A * | 12/1998 | Semel | 604/82 |
| 6,231,559 | B1 | 5/2001 | Loretti | |
| 2004/0134802 | A1 | 7/2004 | Inoue et al. | |

FOREIGN PATENT DOCUMENTS

| | | | |
|---|---|---|---|
| JP | 63-317481 | A | 12/1988 |
| JP | 9-324798 | A | 12/1997 |
| JP | 9-327498 | A | 12/1997 |
| JP | 2002-136570 | A | 5/2002 |
| WO | WO 99/24086 | * | 11/1997 |
| WO | WO 99/24086 | A1 | 5/1999 |
| WO | WO 2004/047714 | * | 6/2004 |
| WO | WO 2004/047714 | A1 * | 6/2004 |

* cited by examiner

*Primary Examiner* — Tatyana Zalukaeva
*Assistant Examiner* — Ilya Treyger
(74) *Attorney, Agent, or Firm* — Sughrue Mion, PLLC

(57) ABSTRACT

In order to provide a medical liquid container which allows for no forgetful failure to open the partition wall and can realize simple and easy sterilization of the liquid medicament bag and thereby decrease the production cost, the present invention provides a medical liquid container having a plurality of communicatably partitioned medical liquid-housing chambers and a discharge reserve chamber having formed therein a discharge port for a liquid medicament, the medical liquid container comprising liquidtightly partitioning portion for liquidtightly separating said liquid medicament-housing chambers from each other, and non-liquidtightly partitioning portion for non-liquidtightly separating between at least one of said liquid medicament-housing chambers and said discharge reserve chamber.

8 Claims, 7 Drawing Sheets

MEDICAL LIQUID CONTAINER

CROSS-REFERENCE TO RELATED APPLICATIONS

This application claims the benefit pursuant to 35 U.S.C. §119 (e) of U.S. Provisional Application No. 60/580,908 filed on Jun. 21, 2004, and priority is claimed from Japanese Patent Application No. 2004-164770 filed Jun. 2, 2004, and U.S. Provisional Application 60/580,908 filed on Jun. 21, 2004, the contents of which are incorporated herein by reference.

TECHNICAL FIELD

The present invention relates to a medical liquid container for housing a liquid medicament, more specifically, a medical liquid container with a plurality of partitioned chambers for housing liquid medicaments.

BACKGROUND ART

There is known a medical liquid container where two or more liquid medicaments are individually housed in partitioned liquid medicament-housing chambers and the liquid medicaments are mixed on use by opening the partition wall separating these liquid medicament-housing chambers and used for drip infusion and the like. Such a medical device of housing a plurality of liquid medicaments individually in liquid medicament-housing chambers partitioned by a partition wall and opening the partition wall on use is being widely used because of its advantageous merits such as reduction of malpractice, prevention of contamination by bacteria at the preparation of a liquid medicament, and enhanced efficiency in the operation for preparing a liquid medicament. However, in the actual medical site, a trouble of administering an incomplete liquid medicament to a patient by forgetfully not opening the partition wall is generated. For the purpose of preventing such a trouble, a medical liquid container with a discharge reserve chamber having formed therein a discharge port for a liquid medicament so as to unfailingly mix two or more liquid medicaments on use is known as the medical liquid container having a plurality of medical liquid-housing chambers.

For example, JP-A-9-327498 (the term "JP-A" as used herein means an "unexamined published Japanese patent application") describes a medical liquid container comprising a plurality of liquid medicament-housing chambers and a discharge reserve chamber, wherein the partition wall separating the plurality of liquid medicament-housing chambers from each other is opened earlier than the partition wall separating the liquid medicament-housing chamber and the discharge reserve chamber and thereby two or more liquid medicaments are unfailingly mixed on use.

JP-A-2002-136570 also similarly describes a medical liquid container wherein upon pressing the liquid medicament-housing chambers, the partition wall separating the liquid medicament-housing chambers from each other is opened earlier than the partition wall separating the liquid medicament-housing chamber and the discharge reserve chamber and thereby two or more liquid medicaments are unfailingly mixed.

The liquid medicament bag containing a liquid medicament in the liquid medicament-housing chamber of a medical liquid container is subjected to a heat sterilization treatment with high-temperature steam so as to guarantee the sterile state within the liquid medicament-housing chamber. When the medical liquid containers disclosed in JP-A-9-327498 and JP-A-2002-136570, where a liquid medicament is filled in the liquid medicament-housing chamber, are sterilized by a heat sterilization treatment, moisture or the like is not present in the discharge reserve chamber and therefore, insufficient sterilization may result after a heat sterilization treatment performed under the same conditions as those for the liquid medicament-housing chamber. In order to overcome such a trouble, the discharge reserve chamber must be sterilized by a radiation or chemical treatment separately from the heat sterilization of the liquid medicament-housing chamber, but this gives rise to a problem that the production process of the liquid medicament bag is complicated and the production cost rises.

The present invention has been made under these circumstances and an object of the present invention is to provide a medical liquid container which allows for no forgetful failure to open the partition wall and can realize simple and easy sterilization of the liquid medicament bag and thereby decrease the production cost.

DISCLOSURE OF THE INVENTION

In order to achieve the above-described object, the present invention provides a medical liquid container having a plurality of communicatably partitioned liquid medicament-housing chambers and a discharge reserve chamber having formed therein a discharge port for a liquid medicament, the medical liquid container comprising liquidtightly partitioning portion for liquidtightly separating the liquid medicament-housing chambers from each other, and non-liquidtightly partitioning portion for non-liquidtightly separating between at least one of the liquid medicament-housing chambers and the discharge reserve chamber.

The liquidtightly partitioning portion may be sufficient if it yields a communicated state resulting from pressure rise in the liquid medicament-housing chamber. The non-liquidtightly partitioning portion may also yield a communicated state by utilizing the pressure rise in the liquid medicament-housing chamber. Furthermore, the liquidtightly partitioning portion and the non-liquidtightly partitioning portion both may yield a communicated state by utilizing the pressure rise in the liquid medicament-housing chamber. The non-liquidtightly partitioning portion is sufficient if it does not yield a communicated state by such a pressure rise in the liquid medicament-housing chamber as causes the liquidtightly partitioning portion to start allowing for communication. The liquidtightly partitioning portion may comprise a peelable seal.

The non-liquidtightly partitioning portion may be a peelable seal, an isolation membrane rupturable by pressure rise in the liquid medicament-housing chamber, or a blocking plug capable of blocking or unblocking the communication opening, each having a pore hole allowing for permeation of a slight amount of the liquid medicament or water content in the liquid medicament. Also, the non-liquidtightly partitioning portion may comprise a seal obtained by interposing a liquid-permeable and/or moisture-permeable material between peelable seal materials.

BEST MODE FOR CARRYING OUT THE INVENTION

Figure 1:
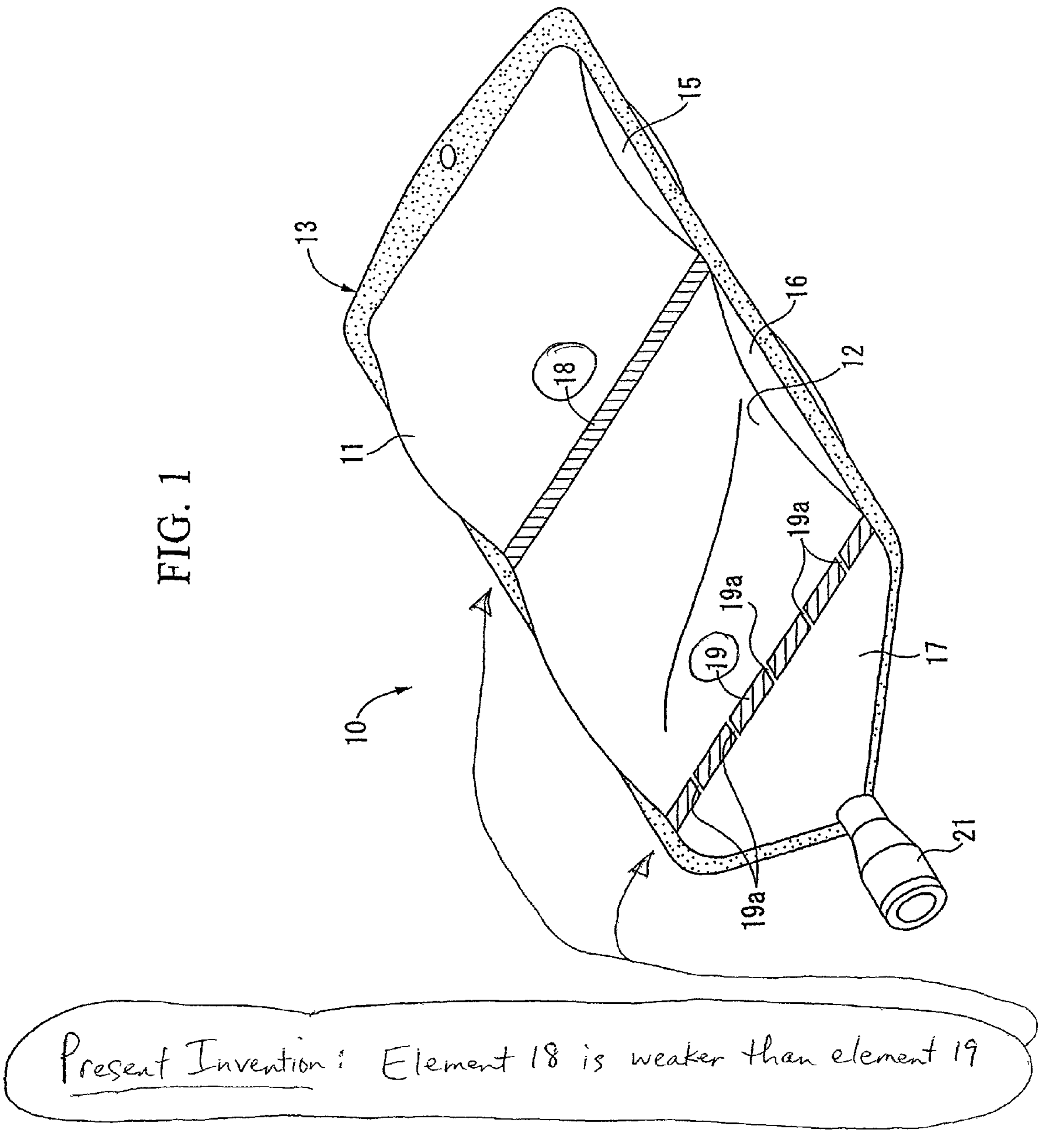
FIG. 1 is an outer appearance perspective view showing a liquid medicament bag where a liquid medicament for medical treatment is filled in the medical liquid container of the present invention.

The embodiment of the present invention is described below by referring to the drawings. FIG. 1 is an outer appearance perspective view showing one example of a liquid medicament bag where a liquid medicament for medical treatment is filled in the medical liquid container of the present invention. The liquid medicament bag 10 comprises, for example, two kinds of liquid medicaments, that is, a first liquid medicament 11 and a second liquid medicament 12, and a medical liquid container 13 for separately housing these liquid medicaments 11 and 12.

The medical liquid container 13 is formed from a synthetic resin film with the circumferential edge part being non-peelably sealed. The resin used for the synthetic resin film is not particularly limited as long as it is a resin used in the field of medical container. Specific examples thereof include a polyolefin resin, a polyamide resin, a polyester resin, a (meth) acrylic resin, a vinyl chloride resin, a vinylidene chloride resin, a polyethersulfone and an ethylene-vinyl alcohol copolymer. Among these, a polyolefin resin is preferred because this is inexpensive and excellent in the transparency, flexibility and hygiene.

Examples of the polyolefin resin include a polyethylene-based resin such as high-density polyethylene, medium-density polyethylene, high-pressure low-density polyethylene, linear low-density polyethylene and ethylene-vinyl acetate copolymer, an olefin-based elastomer such as ethylene-α-olefin random copolymer, a polypropylene-based resin such as polypropylene, ethylene-propylene random copolymer and α-olefin-propylene random copolymer, a cyclic polyolefin resin, and a single-layer or multilayer film comprising a mixture of these resins. Such a resin may be partially crosslinked for the purpose of enhancing heat resistance or the like. This synthetic resin film may have a thickness of 50 to 1,000 μm, preferably on the order of 100 to 500 μm.

The medical liquid container 13 is partitioned into a first liquid medicament-housing chamber 15, a second liquid medicament-housing chamber 16 and a discharge reserve chamber 17. The first liquid medicament 11 and the second liquid medicament 12 are housed in the first liquid medicament-housing chamber 15 and the second liquid medicament-housing chamber 16, respectively. These first liquid medicament-housing chamber 15 and second liquid medicament-housing chamber 16 are separated by a liquidtight seal 18 which is liquidtightly partitioning portion peelable to allow for communication.

The liquidtight seal 18 is peeled off by pressing the first liquid medicament-housing chamber 15 or second liquid medicament-housing chamber 16 to elevate the inner pressure of the first liquid medicament-housing chamber 15 or second liquid medicament-housing chamber 16, as a result, the first liquid medicament-housing chamber 15 and the second liquid medicament-housing chamber 16 are integrated. In this way, when the liquidtight seal 18 is peeled off, the first liquid medicament 11 and the second liquid medicament 12 housed in the first liquid medicament-housing chamber 15 and the second liquid medicament-housing chamber 16, respectively, are mixed.

Examples of the method for forming such a liquidtight seal 18 include a method where a synthetic resin film having formed thereon a layer comprising a composition of resins differing in the melting point or compatibility, such as a mixture of polyethylene and polypropylene, is used for the inner surface side of the medical liquid container 13 and sealed at a temperature lower than the melting temperature of the high melting point resin. Other preferred examples include a method of performing the heat-sealing at a low temperature and effecting weak adhesion in the half melt-bonded state, a method of using a flexible material previously crosslinked by electron beam for the portion where the liquidtight seal 18 is formed, a method of using a seal bar capable of generating a strongly sealed portion at a specific area ratio, and a method of interposing an easily peelable resin tape between two flexible material sheets.

The second liquid medicament-housing chamber 16 and the discharge reserve chamber 17 are separated by a non-liquidtight seal 19 which is non-liquidtightly partitioning portion. In the non-liquidtight seal 19, a pore hole 19*a* penetrating between the second liquid medicament-housing chamber 16 and the discharge reserve chamber 17 is partially formed. One or multiple pore hole(s) 19*a* may be formed. In the example shown, the part unsealed at the production of the non-liquidtight seal 19 forms the pore hole 19*a*. When the first liquid medicament-housing chamber 15 and the second liquid medicament-housing chamber 16 are in the state of being not pressurized, this pore hole 19*a* plays a role of leaking a slight amount of the second liquid medicament 12 housed in the second liquid medicament-housing chamber 16 or water content in the second liquid medicament and introducing it into the discharge reserve chamber 17.

Alternatively, the pore hole 19*a* plays a role of passing the water content in the liquid medicament 12 and introducing it in a state of steam or liquid into the discharge reserve chamber 17 at the high-pressure steam sterilization. Therefore, not only a pore hole is merely formed but also the hole may be filled with a liquid-permeable or moisture-permeable material capable of passing the second liquid medicament 12 or water content in a state of steam or liquid into the discharge reserve chamber 17.

When the first liquid medicament-housing chamber 15 or the second liquid medicament-housing chamber 16 is pressed, the liquidtight seal 18 is peeled off by a pressure rise lower than that for peeling the non-liquidtight seal 19, and the first liquid medicament-housing chamber 15 communicates with the second liquid medicament-housing chamber 16. When the chamber resulting from communication of the first liquid medicament-housing chamber 15 with the second liquid medicament chamber is further pressed, the non-liquidtight seal 19 is peeled off to allow for communication therethrough. In order to realize such an operation, the non-liquidtight seal 19 is formed not to allow for communication under an inner pressure at which the liquidtight seal 18 is peeled off and starts allowing for communication.

In the discharge reserve chamber 17, a discharge port 21 is formed. This discharge port 21 is an outlet for taking out a mixed liquid medicament resulting from mixing of the first liquid medicament 11 and the second liquid medicament 12, and special discharging device such as adapter or needle to take out the mixed liquid medicament from the medical liquid container 13 is connected thereto. The discharge port is sometimes used also as an inlet for mixing and injecting another liquid medicament to the mixed liquid medicament.

Figures 2A, 2B, 2C:
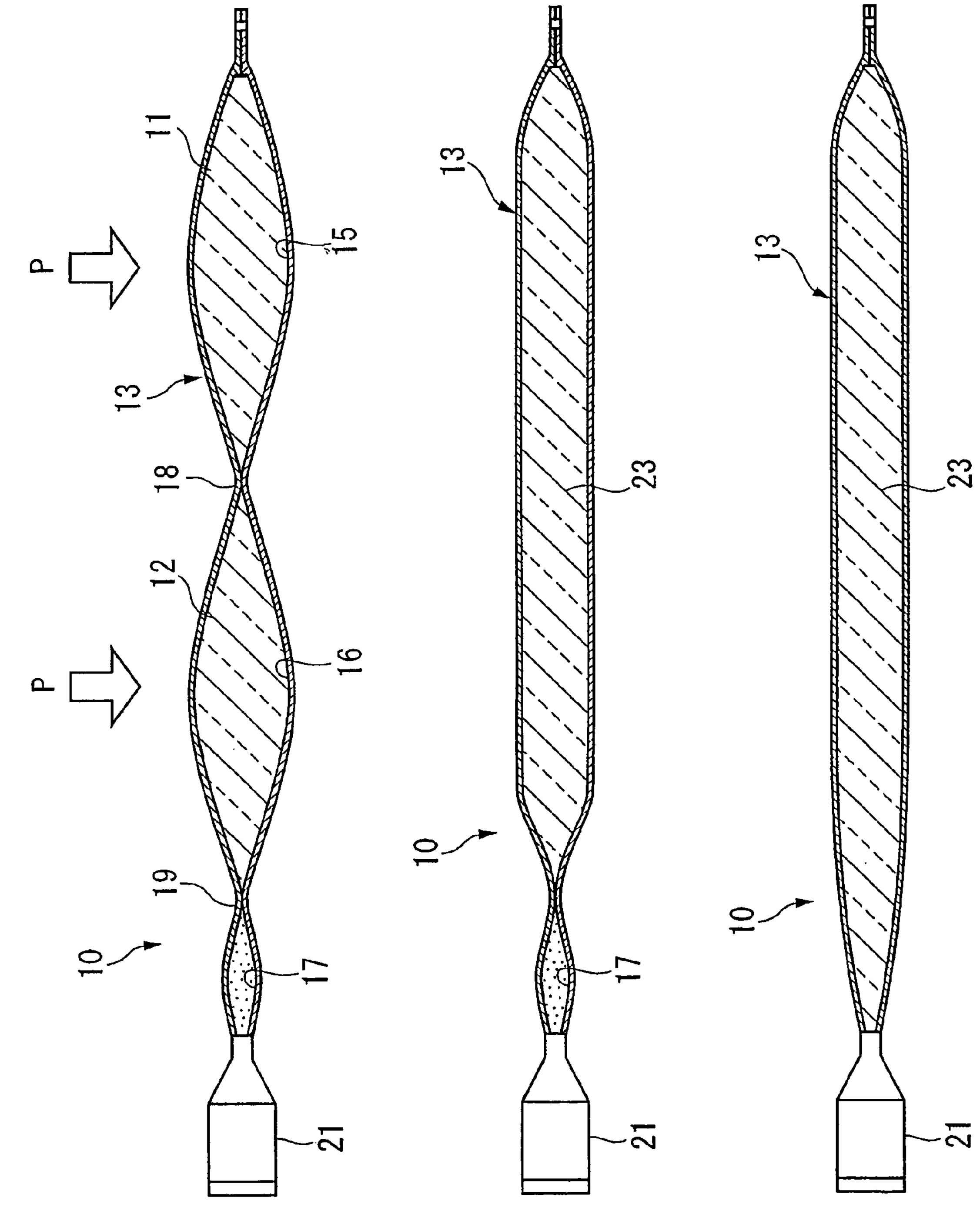
FIGS. 2A to 2C are explanatory views showing the use process of the liquid medicament bag shown in FIG. 1.

On use of the liquid medical bag 10 having the above-described constitution, as shown in FIG. 2A, the first liquid medicament-housing chamber 15 or the second liquid medicament-housing chamber 16 is pressed in the direction of the arrow P to elevate the pressure in the first liquid medicament-housing chamber 15 or second liquid medicament-housing chamber 16. As a result, the liquidtight seal 18 peelable by a pressure rise lower than that for peeling off the non-liquidtight seal 19 is first peeled off, and the first liquid medicament-housing chamber 15 and the second liquid medicament-housing chamber 16 are integrated, whereby, as shown in FIG. 2B, a mixed liquid medicament 23 is obtained. When the liquid medicament bag 10 is further pressed, the non-liquidtight seal 19 is peeled off and the mixed liquid medicament 23 flows into the discharge reserve chamber 17, whereby the mixed liquid medicament 23 can be taken out from the discharge port 21 (see, FIG. 2C).

The liquid medicament bag 10 is constituted in this way to cause peeling of the liquidtight seal 18 by a pressure rise lower than that for peeling off the non-liquidtight seal 19 and therefore, unfailingly prevented from first peeling off the non-liquidtight seal 1 before the liquidtight seal 18 is not peeled off and taking out only the second liquid medicament 12 from the discharge port 21.

Also, even if liquid medicament-discharging device is connected to the discharge port 21 without peeling off the liquidtight seal 18, the liquid medicament is not discharged in an amount large enough to permit visual confirmation of discharging of the liquid medicament. Furthermore, the discharge rate at the start of using the liquid medicament bag 10 cannot be controlled only by the liquid medicament in the discharge reserve chamber 17. In addition, although the lower part in the vicinity of the discharge port is bulged when the liquid medicament bag after allowing respective chambers to communicate with each other to give a mixed liquid medicament is hung by directing downward the discharge port 21 on use, the liquid medicament bag 10 failing in communication of the discharge reserve chamber 17 with another chamber is thin because only a very small amount of the liquid medicament is contained in the discharge reserve chamber 17, and when the liquid medicament bag 10 is hung by directing downward the discharge port 21, it is easy to notice that these chambers are not communicated with each other.

As described above, the medical liquid container of the present invention reminds the user of forgetful non-communication before actual use and therefore, it can be unfailingly prevented to take out only the second liquid medicament 12 from the discharge port 21 and also to generate substantially no discharge of the liquid medicament.

The operation of the medical liquid container of the present invention is described below by referring to FIGS. 1 and 3. The liquid medicament bag 10 housing a first liquid medicament 11 and a second liquid medicament 12 in the medical liquid container 13 must be assured of sterility at the production. The liquid medicament bag 10 is heated, for example, with a high-pressure steam S at a sterilization temperature. Such high-pressure steam sterilization is performed, for example, by housing and pressurizing the liquid medicament bag 10 in a pressure container and exposing it to hot water bath, hot water shower or steam for a predetermined time.

Figure 3:
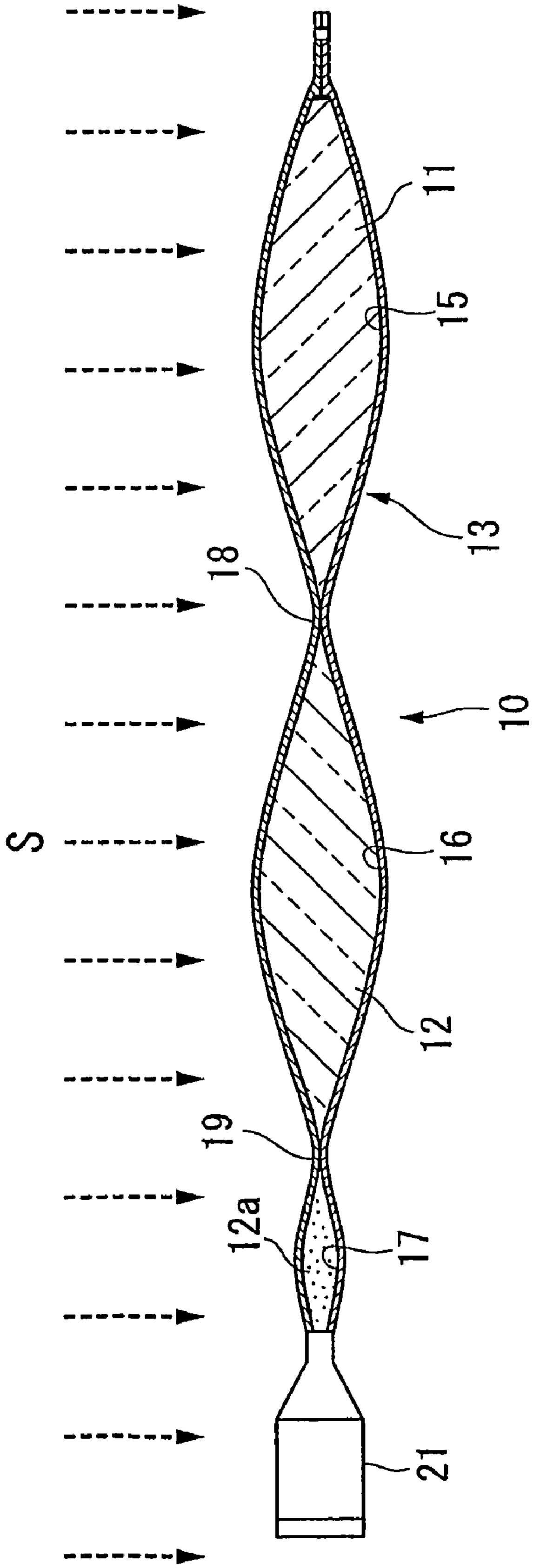
FIG. 3 is an explanatory view for explaining the operation of the medical liquid container of the present invention.

At this high-pressure steam sterilization, a slight amount of the second liquid medicament 12 housed in the second liquid medicament-housing chamber 16 is leaking through a pore hole 19*a* provided in the non-liquidtight seal 19 and flowing into the discharge reserve chamber 17 of the liquid medicament bag 10 and when the discharge reserve chamber 17 is exposed to a high-pressure steam or the like, the water content in this slight amount of inflowed second liquid medicament 12*a* is partially vaporized and spreads over in the entire discharge reserve chamber 17, as shown in FIG. 3, as a result, the pressure therein reaches a saturated water vapor pressure and the sterility assurance level in the discharge reserve chamber 17 is made equal to that of the liquid medicament-housing chamber. Alternatively, at the high-pressure sterilization, the water content in a state of liquid or steam of the second liquid medicament-housing chamber 16 flows through the pore hole 19*a* into the discharge reserve chamber 17 and the pressure therein reaches a saturated water vapor pressure, whereby the sterility assurance level in the discharge reserve chamber 17 is made equal to that of the liquid medicament-housing chamber.

Conventionally known liquid medicament bags with a measure for preventing a forgetful failure to open the partition wall must be subjected to an electron-beam or chemical sterilization treatment so as to sterilize the discharge reserve chamber. However, in the present invention, a non-liquidtight seal 19 is used for the partition wall separating the second liquid medicament-housing chamber 16 and the discharge reserve chamber 17, and a small amount of the second liquid medicament 12 housed in the second liquid medicament-housing chamber 16 or a small amount of the water content in the second liquid medicament is caused to leak out into the discharge reserve chamber 17, so that the sterility assurance level in the discharge reserve chamber 17 can be made equal to that of the liquid medicament-housing chamber by the small amount of inflowed second liquid medicament drops 12*a* at the high-pressure steam sterilization, and a radiation treatment or chemical sterilization treatment exclusively for the discharge reserve chamber can be dispensed with. As a result, simplification of the sterilization step for the medical preparation in the liquid medicament bag and reduction of the production cost can be realized and at the same time, the entire liquid medicament bag with a discharge reserve chamber can be assured of sterility.

The non-liquidtight seal 19 is a seal of allowing for leakage of a small amount of liquid between the second liquid medicament-housing chamber 16 and the discharge reserve chamber 17. With respect to the leakage rate, for example, in the case of use for medical treatment of a patient, the upper limit is a leakage rate insufficient as a dosage per hour for the administration of the mixed liquid medicament to the patient, and the lower limit is a leakage rate of giving a liquid amount large enough to put the discharge reserve chamber 17 and the discharge port 21 into a sterility assurance level equal to the sterility assurance level of the first liquid medicament-housing chamber 15 or the second liquid medicament-housing chamber 16 when high-pressure steam sterilization is performed under the conditions of guaranteeing the sterile state of the first liquid medicament-housing chamber 15 and the second liquid medicament-housing chamber 16.

This leakage rate is, for example, 0.12 mL/min or less, preferably 0.06 mL/min or less, more preferably 0.012 mL/min or less. When the leakage rate is in this range, even if the communication between chambers is forgotten and drip infusion is performed, the dripping rate of drip infusion is only one or two drops per minute and normal drip infusion cannot be performed at this rate. Therefore, it is clearly known that the first liquid medicament-housing chamber 15 and the second liquid medicament-housing chamber 16 are not communicated and mixed with each other.

The lower limit of the leakage rate is a leakage rate which can create a state capable of realizing sterility assurance of the same level among the first liquid medicament-housing chamber 15, the second liquid medicament-housing chamber 16, the discharge reserve chamber 17 and the discharge port 21 when high-pressure steam sterilization is performed under the conditions of putting the liquid medicaments filled in the container, that is, the first liquid medicament 11 in the first liquid medicament-housing chamber 15 and the second liquid medicament 12 in the second liquid medicament-housing chamber 16, into a necessary sterility assurance level, or which can permit the water content in a state of liquid or water vapor to leak out, in an amount large enough to ensure at least a sterility assurance level of 1-6 or less for the discharge reserve chamber and the discharge port, from the liquid medicament-housing chamber into the spatial part comprising the discharge reserve chamber and the discharge port until high-pressure steam sterilization is performed.

This leakage rate varies depending on various conditions such as production or storage state of the medicament-containing medical liquid container, time period after filling of the liquid medicament until high-pressure steam sterilization, and temperature and time of the high-pressure steam sterilization, and cannot be specified as a value but can be defined by the necessary amount of the water content which should be present in the discharge reserve chamber and the discharge port at the high-pressure steam sterilization in order to fill the discharge reserve chamber and the discharge port with a saturated water vapor and create an effectively heat sterilizable state at a maximum temperature achievable during the high-pressure steam sterilization.

Specifically, the amount of water content can be determined by using Attached Table 1.1: Saturated Water Vapor Pressure Obtained from Saturated Steam of Water described in "Humidity-Measuring Method" of JIS Z 8806, and Interpretative Table 1: Formula ($d_V$=e·$M_V$·RT) of Reducing Water Vapor Pressure e into Absolute Humidity $d_V$ in Conversion Formula for the Amount Representing Humidity. Assuming that the maximum temperature at the high-pressure steam sterilization is 130.0° C., when a saturated water vapor pressure $e_S$=270.3 kPa obtained from Attached Table 1.1 is employed and an absolute temperature T (t/° C.=T/K−273.15) defined in the same JIS Z 8806, a gas constant R=8.314472 $J{\cdot}K^{-1}{\cdot}mol^{-1}$ and a water molar mass $M_V$=18.01528 kg/mol are applied to the Conversion Formula of Interpretative Table 1, the amount of liquid necessary to be present in the discharge reserve chamber 17 and the discharge port 21 at the high-pressure steam sterilization treatment so as to ensure a sterile state for the internal spatial part comprising the discharge reserve chamber and the discharge port is about 2 mg/$cm^3$ per the spatial amount. In other words, it is sufficient if a medicament containing 2 μL/$cm^3$ of water is present.

More specifically, for example, assuming that the spatial amount of the discharge reserve chamber is 30 $cm^3$, the required water amount is about 60 μL. Also, since one drop at the drip infusion is presumed to be about 60 μL, by using a water content amount on the order of one medicament drop, the space in the discharge reserve chamber and discharge port is expected to be filled with a saturated water vapor at the high-pressure steam sterilization. Furthermore, the maximum spatial amount of the discharge reserve chamber is about 120 $cm^3$ and therefore, it is sufficient if four or more drops are present in the discharge reserve chamber after the high-pressure steam sterilization.

The sterility assurance can be defined by the method described in the English translation of The Japanese Pharmacopoeia Fourteenth Edition, General Information, 15 Terminal Sterilization and Sterilization Indicators. Specifically, the same method as that used for verifying the sterility assurance of liquid medicament can be employed. In one example of the evaluation method, for example, when an over kill method is employed, a paper strip-type biological indicator containing a known number of *Bacillus stearothermophilus* spores available as ATCC 7953 having a D-value of 1 or more is used as the sterilization indicator, and this indicator is placed in the discharge reserve chamber. In the case of a large discharge reserve chamber, multiple indicators are dispersedly placed.

In the case of placing multiple biological indicators, examples of the position where the indicators are placed include the corners and center of the portion formed of film in the discharge reserve chamber, and the inside of the discharge port portion. It is important to confirm that the cold spots in the discharge reserve chamber, where the saturated water vapor is hardly reachable at the high-pressure steam sterilization, are also sterilized.

In this state, high-pressure steam sterilization is performed under the conditions of assuring sterility of the liquid medicament-housing chamber, and how many spores on the biological indicator are decreased is examined. When the decrease in the power of 12 results, this means that a sterility assurance level of $10^{-6}$ or less is obtained.

Figure 4:
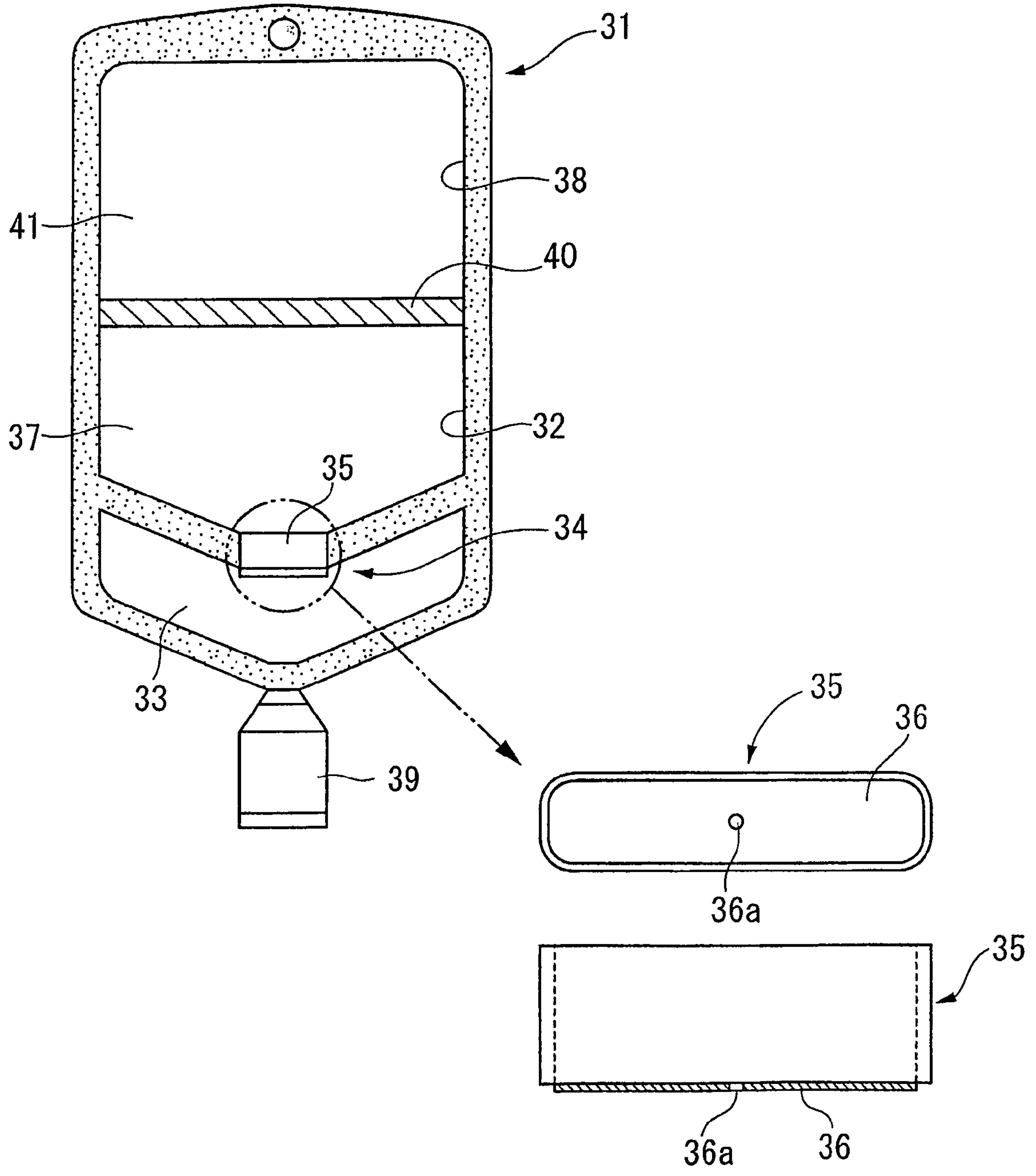
FIG. 4 is an explanatory view showing another embodiment of the medical liquid container of the present invention.

As for the non-liquidtight seal (non-liquidtightly partitioning portion) separating the second liquid medicament-housing chamber and the discharge reserve chamber, other than the above-described embodiment, for example, a partitioning member may be formed therein as shown in FIG. 4. In the medical liquid container 31 shown in FIG. 4, a partitioning member 35 is provided in the non-liquidtight seal (non-liquidtightly partitioning member) 34 separating the second liquid medicament-housing chamber 32 and the discharge reserve chamber 33. The seal parts on both sides of the partitioning member 35 are an unpeelable seal part. The partitioning member 35 is formed of, for example, a flexible resin, and an isolation membrane 36 is provided over the entire surface thereof. Furthermore, a pore hole 36*a* for allowing a slight amount of the second liquid medicament 37 housed in the second liquid medicament-housing chamber 32 to leak out into the discharge reserve chamber 33 is formed in the isolation membrane 36.

Also in such a medical liquid container 31, a slight amount of the second liquid medicament 37 flows into the discharge reserve chamber 33 through the pore hole 36*a* and therefore, a sterility assurance level equal to that of the liquid medicament-housing chamber can be ensured for the discharge reserve chamber 33 and the discharge port 39 at the high-pressure steam sterilization treatment by virtue of the steam from the slight amount of inflowed second liquid medicament 37. Alternatively, the pore hole 36*a* plays a role of passing the water content in the liquid medicament and introducing it in a state of steam or liquid into the discharge reserve chamber 33 at the high-pressure steam sterilization. Therefore, not only a pore hole is merely formed but also the hole may be filled with a liquid-permeable or moisture-permeable material capable of passing the second liquid medicament 12 or water content in a state of steam or liquid into the discharge reserve chamber 33.

This isolation membrane 36 of the medical liquid container 31 may be sufficient if it is formed to have a strength larger than the peel strength of the liquidtight seal (liquidtightly partitioning portion) 40 separating the first liquid medicament-housing chamber 38 and the second liquid medicament-housing chamber 32. By forming in this way, when the first liquid medicament-housing chamber 38 or second liquid medicament-housing chamber 32 is pressed on use, the liquidtight seal 40 is first peeled off, and the first liquid medicament 41 and the second liquid medicament 37 are mixed to form a mixed liquid medicament. When the first liquid medicament-housing chamber 38 or second liquid medicament-housing chamber 32 is further pressed, the isolation membrane 36 is ruptured by the mixed liquid medicament, as a result, the mixed liquid medicament can be taken out from the discharge port 39.

Figure 5:
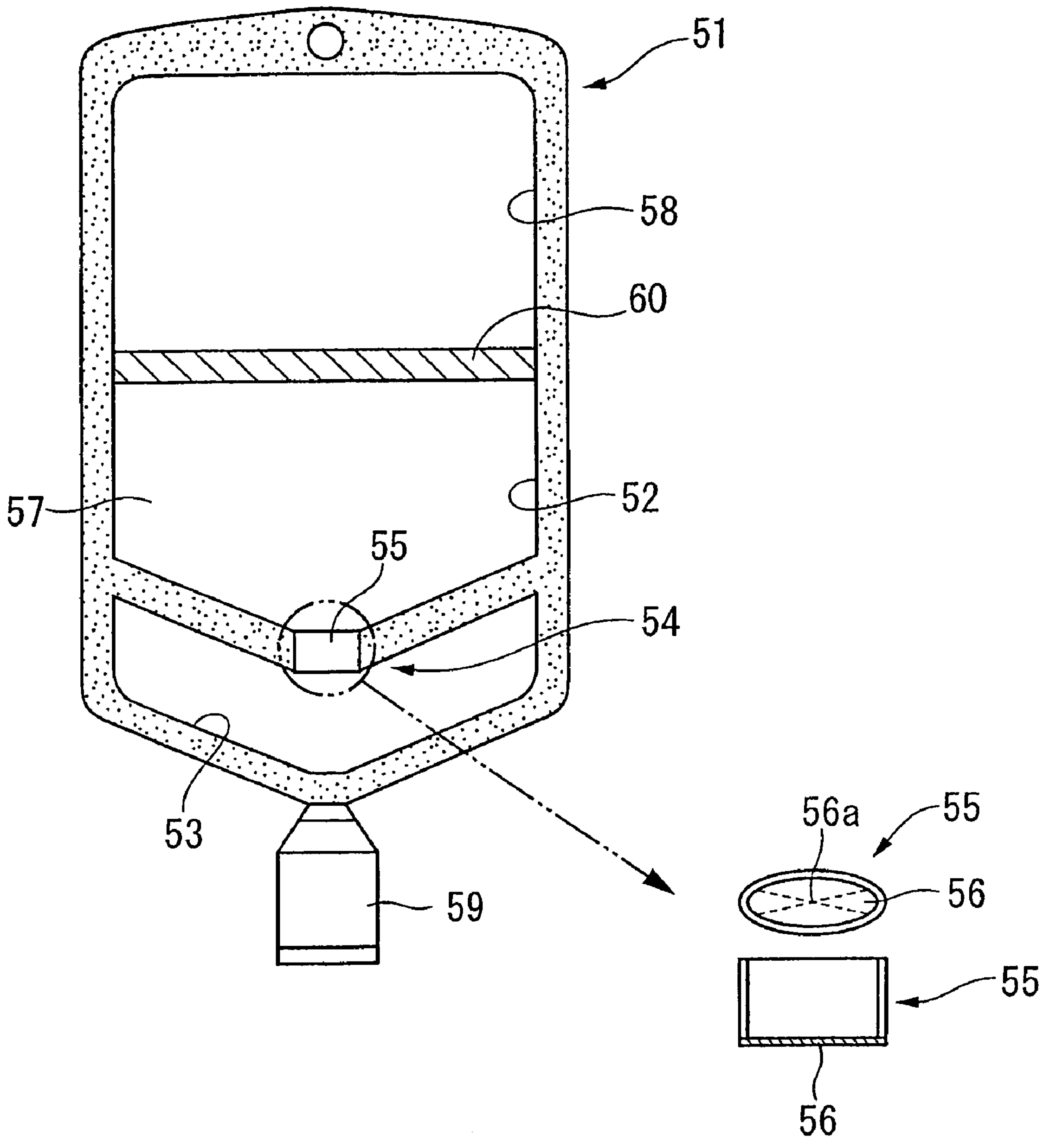
FIG. 5 is an explanatory view showing still another embodiment of the medical liquid container of the present invention.

As for the non-liquidtight seal (non-liquidtightly partitioning portion) separating the second liquid medicament-housing chamber and the discharge reserve chamber, for example, a cylindrical partitioning member may be formed therein as shown in FIG. 5.

In the medical liquid container 51 shown in FIG. 5, a partitioning member 55 is provided in the non-liquidtight seal (non-liquidtightly partitioning member) 54 separating the second liquid medicament-housing chamber 52 and the discharge reserve chamber 53. The partitioning member 55 is formed of, for example, a flexible resin, and a thin resin film (isolation membrane) 56 is provided over the entire surface thereof. Furthermore, a pore hole 56*a* for allowing a slight amount of the second liquid medicament 57 housed in the second liquid medicament-housing chamber 52 to leak out into the discharge reserve chamber 53 is formed in the resin film 56. Also, the pore hole 56*a* may be formed as perforations to take a part of facilitating the rupture.

Also in such a medical liquid container 51, a slight amount of the second liquid medicament 57 flows into the discharge reserve chamber 53 through the pore hole 56*a* and therefore, a sterility assurance level equal to that of the liquid medicament-housing chamber can be ensured for the discharge reserve chamber 53 and the discharge port 59 at the high-pressure steam sterilization treatment by virtue of the steam from the slight amount of inflowed second liquid medicament 57. Alternatively, the pore hole 56*a* plays a role of passing the water content in the liquid medicament and introducing it in a state of steam or liquid into the discharge reserve chamber 53 at the high-pressure steam sterilization. Therefore, a liquid-permeable or moisture-permeable material may be used in place of the film with a pore hole.

Furthermore, also in such a medical liquid container 51, the resin film 56 is formed to have a rupture strength larger than the peel strength of the liquidtight seal (liquidtightly partitioning portion) 60 separating the first liquid medicament-housing chamber 58 and the second liquid medicament-housing chamber 52. When the first liquid medicament-housing chamber 58 or second liquid medicament-housing chamber 52 is pressed on use, the liquidtight seal 60 is first peeled off to form a mixed liquid medicament and thereafter, when the first liquid medicament-housing chamber 58 or second liquid medicament-housing chamber 52 is further pressed, the resin film 56 is ruptured by the mixed liquid medicament, as a result, the mixed liquid medicament can be taken out from the discharge port 59.

Figure 6A:
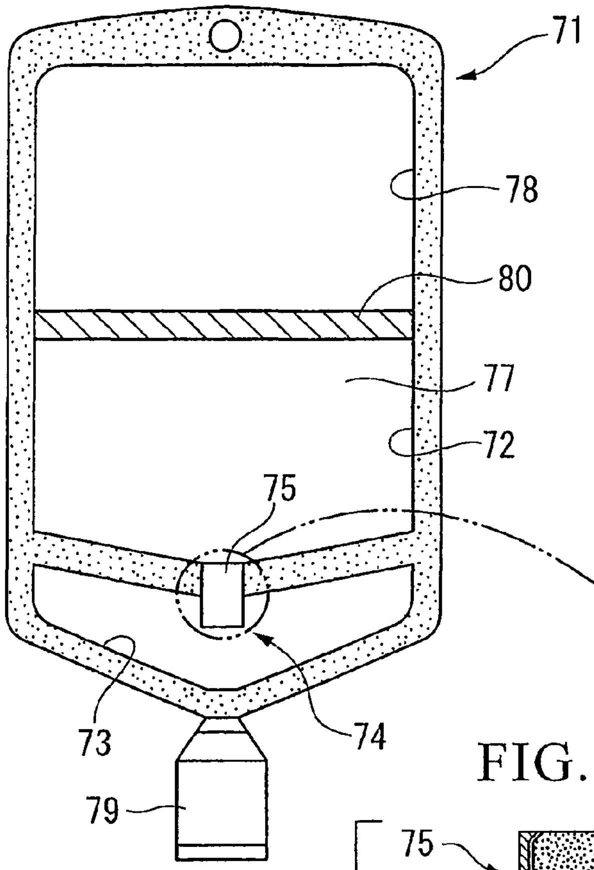
FIGS. 6A to 6C are explanatory views showing still another embodiment of the medical liquid container of the present invention.
Figure 6B:
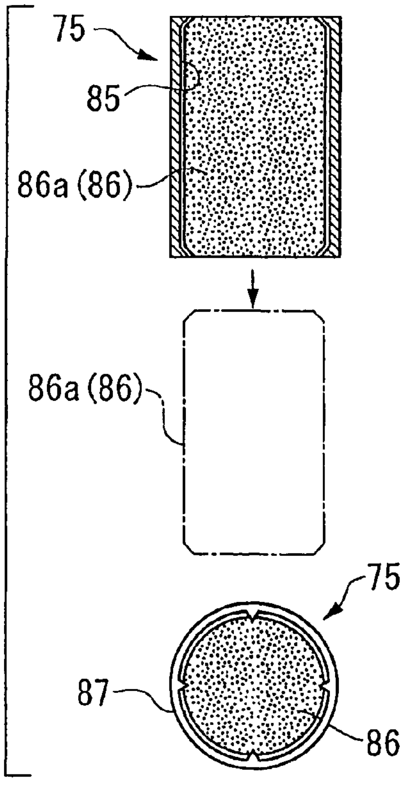
Figure 6C:
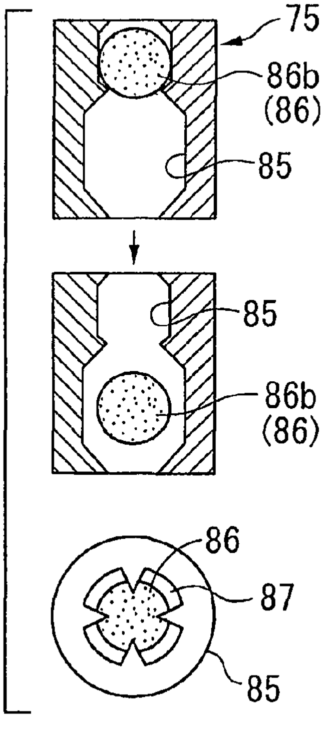

As shown in FIG. 6, the non-liquidtight seal (non-liquidtightly partitioning portion) separating the second liquid medicament-housing chamber and the discharge reserve chamber may have, for example, a blocking plug. In the medical liquid container 71 shown in FIG. 6A, a blocking member 75 is provided in the non-liquidtight seal (non-liquidtightly partitioning member) 74 separating the second liquid medicament-housing chamber 72 and the discharge reserve chamber 73. The blocking member 75 comprises a cylindrical communication opening 85 and a blocking plug 86 for blocking the communication opening 85. Examples of the shape of the blocking member 75 include those where a cylindrical blocking plug 86*a* is blocking the communication opening 85 as shown in FIG. 6B or a spherical blocking plug 86*b* is blocking the communication opening 85 as shown in FIG. 6C.

Also in such a medical liquid container 71, a slight amount of the second liquid medicament 77 inflows through a fine gap 87 between the communication opening 85 and the blocking plug 86 and therefore, a sterility assurance level equal to that of the liquid medicament-housing chamber can be ensured for the discharge reserve chamber 73 and the discharge port 79 at the high-pressure steam sterilization treatment by virtue of the steam from the slight amount of inflowed second liquid medicament 77. Alternatively, the fine gap between the communication opening 85 and the blocking plug 86 plays a role of passing the water content in the liquid medicament and introducing it in a state of steam or liquid into the discharge reserve chamber 73 at the high-pressure steam sterilization.

Furthermore, also in such a medical liquid container 71, the communication opening 85 and the blocking plug 86 are engaged at a strength larger than the peel strength of the liquidtight seal (liquidtightly partitioning portion) 80 separating the first liquid medicament-housing chamber 78 and the second liquid medicament-housing chamber 72. When the first liquid medicament-housing chamber 78 or second liquid medicament-housing chamber 72 is pressed on use, the liquidtight seal 80 is first peeled off to form a mixed liquid medicament and thereafter, when the first liquid medicament-housing chamber 78 or second liquid medicament-housing chamber 72 is further pressed, the blocking plug 86 in the communication opening 85 is pushed by the mixed liquid medicament and removed from the communication opening 85, as a result, the mixed liquid medicament can be taken out from the discharge port 79.

Figure 7:
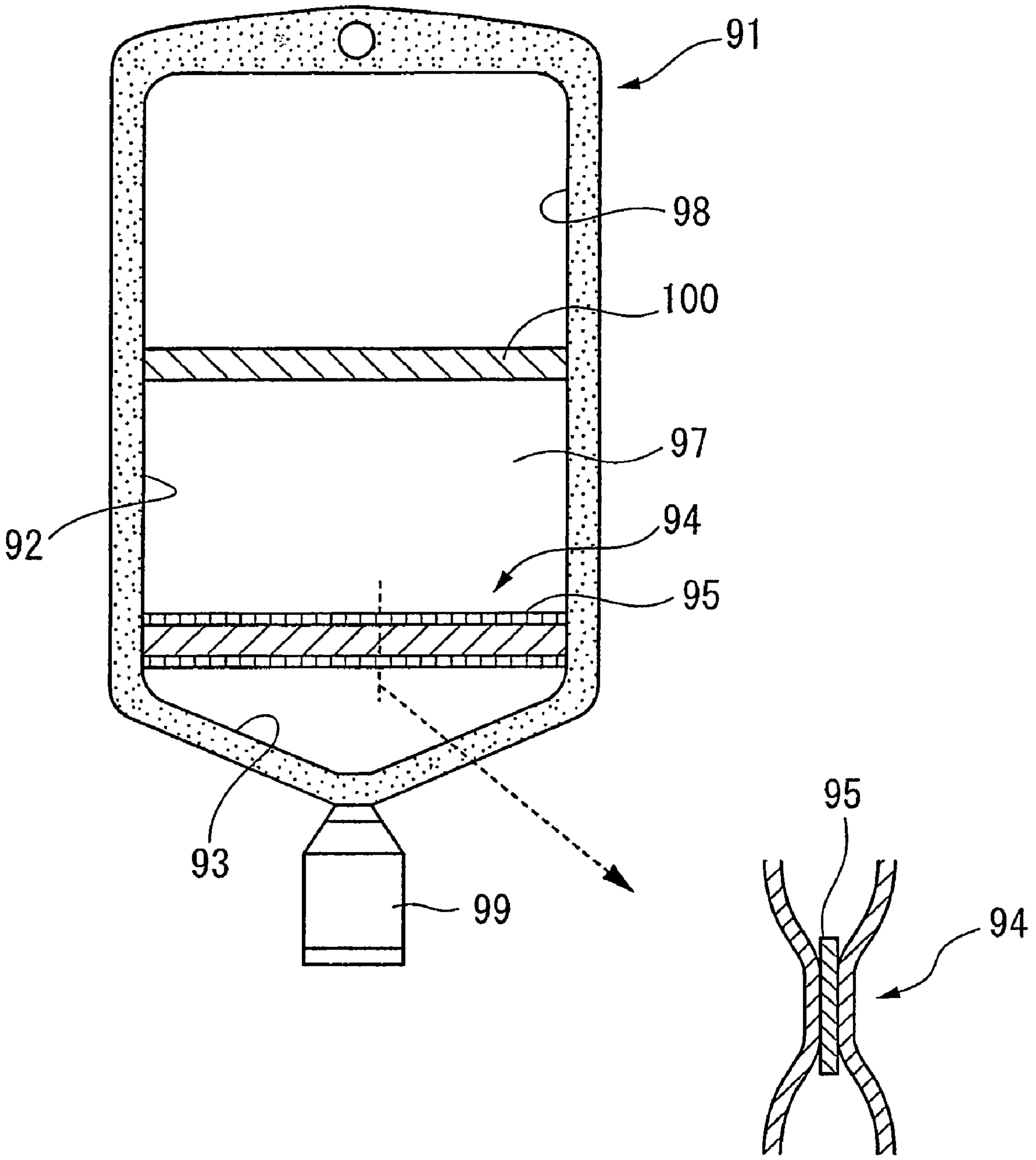
FIG. 7 is an explanatory view showing still another embodiment of the medical liquid container of the present invention.

As shown in FIG. 7, the non-liquidtight seal (non-liquidtightly partitioning portion) separating the second liquid medicament-housing chamber and the discharge reserve chamber may be, for example, a seal prepared by interposing a liquid-permeable or moisture-permeable material between peelable seals. The liquid-permeable or moisture-permeable material is not particularly limited, but examples thereof include sterilized paper, porous non-woven fabric comprising high-density polyethylene fiber, and cellulose-mixed polyester.

In the medical liquid container 91 shown in FIG. 7, a sterilized paper 95 is interposed in the non-liquidtight seal (non-liquidtightly partitioning portion) 94 separating the second liquid medicament-housing chamber 92 and the discharge reserve chamber 93. Also in such a medical liquid container 91, a slight amount of the second liquid medicament 97 inflows through the sterilized paper 95 having liquid or moisture permeability and therefore, a sterility assurance level equal to that of the liquid medicament-housing chamber can be ensured for the discharge reserve chamber 93 and the discharge port 99 at the high-pressure steam sterilization treatment by virtue of the steam from the slight amount of inflowed second liquid medicament 97.

When the first liquid medicament-housing chamber 98 or second liquid medicament-housing chamber 92 is pressed on use, the liquidtight seal 100 is first peeled off to form a mixed liquid medicament and thereafter, when the first liquid medicament-housing chamber 98 or second liquid medicament-housing chamber 92 is further pressed, the non-liquidtight seal (non-liquidtightly partitioning portion) 94 is pealed off by the mixed liquid medicament, as a result, the mixed liquid medicament can be taken out from the discharge port 99.

INDUSTRIAL APPLICABILITY

According to the medical liquid container of the present invention, a slight amount of the liquid medicament housed in the liquid medicament-housing chamber or water content in the liquid is leaking and flowing into the discharge reserve chamber through the non-liquidtightly partitioning member, and the water content in the liquid medicament flowed in a small amount into the discharge reserve chamber is vaporized under heat of the high-pressure steam at the high-pressure steam sterilization treatment and spreads over in the entire discharge reserve chamber, so that the discharge reserve chamber can be put into a state of sterility assurance level equal to the liquid medicament-housing chamber by sterilization under the same conditions as those in the heat sterilization of the liquid medicament-housing chamber.

Conventionally known liquid medicament bags with a measure for preventing a forgetful failure to open the partition wall must be subjected to a radiation treatment with electron beam, γ ray or the like, or a chemical sterilization treatment with ethylene oxide gas, formaldehyde gas or the like, so as to sterilize the discharge reserve chamber. However, in the present invention, non-liquidtightly partitioning portion is used for the partition wall separating the liquid medicament-housing chamber and the discharge reserve chamber, and a small amount of water content in the liquid medicament housed in the liquid medicament-housing chamber is caused to leak out into the discharge reserve chamber, so that the discharge reserve chamber can be sterilized by this small amount of inflowed liquid medicament or water content in the liquid medicament at the high-pressure steam sterilization, and a radiation treatment or chemical sterilization treatment for sterilizing the discharge reserve chamber can be dispensed with. As a result, simplification of the sterilization step for the medical preparation in the liquid medicament bag and reduction of the production cost can be realized and at the same time, sterility assurance of the entire liquid medicament bag with a discharge reserve chamber allowing for no forgetful failure to open the partition wall can be obtained.

The invention claimed is:

1. A medical liquid container having a plurality of communicatably partitioned medical liquid-housing chambers and a discharge reserve chamber having formed therein a discharge port for a liquid medicament, the medical liquid container comprising liquidtightly partitioning portion for liquidtightly separating said liquid medicament-housing chambers from each other, and non-liquidtightly partitioning portion for non-liquidtightly separating between at least one of said liquid medicament-housing chambers and said discharge reserve chamber, and wherein said non-liquidtightly partitioning portion is a peelable seal, an isolation membrane rupturable by a pressure rise in a liquid medicament-housing chamber, or a blocking plug capable of blocking or unblocking the communication opening, each having a pore hole allowing for leaking and flowing of a slight amount of said liquid medicament into said discharge reserve chamber, and wherein a leakage rate for the slight amount of said liquid medicament has an upper limit, which is a leakage rate insufficient as a dosage per hour for the administration of the mixed liquid medicament to the patient, and a lower limit, which is a leakage rate of giving a liquid amount large enough to put the discharge reserve chamber and the discharge port into a sterility assurance level equal to the sterility assurance level of a first liquid medicament-housing chamber or a second liquid medicament-housing chamber when high-pressure steam sterilization is performed under conditions of guaranteeing a sterile state of the first liquid medicament-housing chamber and the second liquid medicament-housing chamber, wherein when the second liquid medicament-housing chamber is pressed, said non-liquidtightly partitioning portion does not yield a communicated state by such a pressure rise in the liquid medicament-housing chamber as causes said liquidtightly partitioning portion to start allowing for communication.

2. The medical liquid container as claimed in claim 1, wherein said liquidtightly partitioning portion and/or non-liquidtightly partitioning portion yield a communicated state resulting from pressure rise in said liquid medicament-housing chamber.

3. The medical liquid container as claimed in claim 1, wherein said non-liquidtightly partitioning portion does not yield a communicated state by such a pressure rise in the liquid medicament-housing chamber as causes said liquidtightly partitioning portion to start allowing for communication.

4. The medical liquid container as claimed in claim 1, wherein said liquidtightly partitioning portion comprises a peelable seal.

5. The medical liquid container as claimed in claim 1, wherein said non-liquidtightly partitioning portion comprises a seal obtained by interposing a liquid-permeable material between peelable seals.

6. A medical liquid container having a plurality of communicatably partitioned medical liquid-housing chambers and a discharge reserve chamber having formed therein a discharge port for a liquid medicament, the medical liquid container comprising liquidtightly partitioning portion for liquidtightly separating said liquid medicament-housing chambers from each other, and non-liquidtightly partitioning portion for non-liquidtightly separating between at least one of said liquid medicament-housing chambers and said discharge reserve chamber, wherein said liquid medicament-housing chambers comprise a first liquid medicament-housing chamber and a second liquid medicament-housing chamber, wherein said second liquid medicament-housing chamber and said discharge reserve chamber are separated by said non-liquidtightly partitioning portion, wherein when the second liquid medicament-housing chamber is pressed, said non-liquidtightly partitioning portion does not yield a communicated state by such a pressure rise in the liquid medicament-housing chamber as causes said liquidtightly partitioning portion to start allowing for communication, wherein the liquidtightly partitioning portion yields a communicated state, and then the non-liquidtightly partitioning portion yields a communicated state.

7. The medical liquid container according to claim 1, wherein a leakage rate of the liquid medicament through the non-liquidtight seal is 0.12 mL/min or less.

8. The medical liquid container according to claim 6, wherein the liquidtightly partitioning portion yields a communicated state, and then the non-liquidtightly partitioning portion yields a communicated state.

* * * * *

UNITED STATES PATENT AND TRADEMARK OFFICE

CERTIFICATE OF CORRECTION

PATENT NO. : 8,157,783 B2
APPLICATION NO. : 11/579325
DATED : April 17, 2012
INVENTOR(S) : Katsuyki Yoshikawa It is certified that error appears in the above-identified patent and that said Letters Patent is hereby corrected as shown below:

Title page, please make the following amendments:

Insert:

-- Related U.S. Application Data

(60) Provisional application No. 60/580,908, filed on June 21, 2004. --.

Item (30) should read:

-- (30) Foreign Application Priority Data

~~June 24, 2004~~June 2, 2004 (JP) P2004-164770 --.

Signed and Sealed this
Twenty-fifth Day of December, 2012

David J. Kappos
*Director of the United States Patent and Trademark Office*